United States Patent [19]

Poler

[11] 4,298,995
[45] Nov. 10, 1981

[54] INTRAOCULAR LENS CONSTRUCTION

[76] Inventor: Stanley Poler, 78 E. Second St., New York, N.Y. 10003

[21] Appl. No.: 147,332

[22] Filed: May 6, 1980

Related U.S. Application Data

[63] Continuation-in-part of Ser. No. 57,323, Jul. 13, 1979, Pat. No. 4,249,271.

[51] Int. Cl.³ .............................. A61F 1/16; A61F 1/24
[52] U.S. Cl. ............................................................ 3/13
[58] Field of Search .......................................... 3/13, 1

[56] References Cited

U.S. PATENT DOCUMENTS

| | | | |
|---|---|---|---|
| 4,056,855 | 11/1977 | Kelman | 3/13 |
| 4,080,709 | 3/1978 | Poler | 3/13 X |
| 4,110,848 | 9/1978 | Jensen | 3/13 |
| 4,159,546 | 7/1979 | Shearing | 3/13 |
| 4,174,543 | 11/1979 | Kelman | 3/13 |
| 4,251,887 | 2/1981 | Anis | 3/13 |

FOREIGN PATENT DOCUMENTS 2717706 10/1978 Fed. Rep. of Germany ............ 3/13
563174 7/1977 U.S.S.R. .................................. 3/13

Primary Examiner—Ronald L. Frinks
Attorney, Agent, or Firm—Hopgood, Calimafde, Kalil, Blaustein & Judlowe

[57] ABSTRACT

The invention contemplates an improved lens implant for use in ophthalmological surgery, the lens being a replacement for a cataract-clouded natural lens, and the replacement being installed via the pupil at the iris as the operative step following removal of cataract material. The invention features flexible haptic structure assembled to and retaining an optically finished lens element. The haptic structure integrally includes two asymmetrically defined generally diametrically opposed stabilizing feet which extend radially outward of the region of lens retention and which are each characterized by an arcuate peripheral band adapted for positioning engagement with structural features within one of the chambers of a human eye. Loop formations local to a single peripheral band and to the region of lens retention define localized openings adapted for reception of suture, pincer or other manipulative instrumentalities.

22 Claims, 7 Drawing Figures

INTRAOCULAR LENS CONSTRUCTION

BACKGROUND OF THE INVENTION

This application is a continuation-in-part of my copending application, Ser. No. 057,323, filed July 13, 1979, now U.S. Pat. No. 4,249,271.

Said application discloses a variety of intraocular-lens constructions featuring different kinds of haptic for specific different types and locations of implantation in a human eye; and the present invention relates particularly to that variety which is adapted for trans-iris manipulation and installation.

Reference is made to said copending application for a more full statement of the background of the invention.

BRIEF STATEMENT OF THE INVENTION

It is an object of the invention to provide an improved intraocular lens and associated haptic of the character indicated.

Another object is to provide such structure with improved features adapting the same for trans-iris manipulation and implantation.

A further object is to meet the above object with a configuration from which a uniquely identifiable orientation can be readily recognized by the surgeon making an intraocular implantation.

The foregoing and other objects and features are realized in a variety of flexible haptic structures wherein two asymmetrically defined, generally diametrically opposed stabilizing feet extend radially outward of the region of lens retention and which are each characterized by an arcuate peripheral band adapted for positioning engagement with structural features within the posterior chamber of the eye. Loop formations local to a single peripheral band and to the region of lens retention define localized openings adapted for reception of suture, pincer or other means.

DETAIL DESCRIPTION

The invention will be described in detail for various embodiments, in conjunction with the accompanying drawings, in which.

Figure 1:
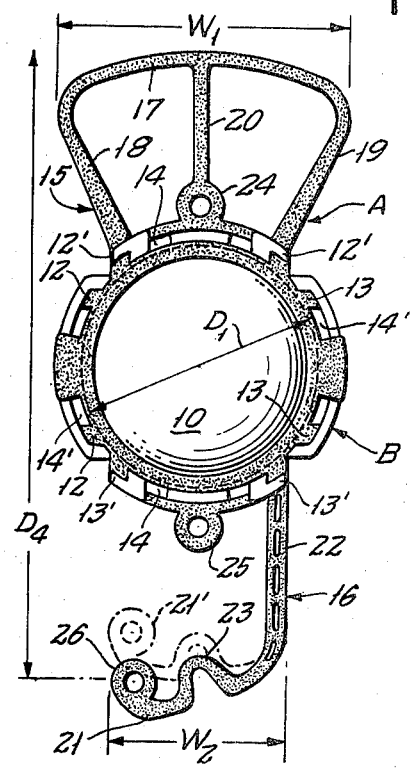
FIG. 1 is a view in elevation, showing an intraocular lens and haptic assembly of the invention.
Figure 2:
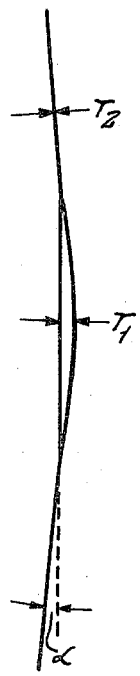
FIG. 2 is a side view of the assembly of FIG. 1.
Figure 3:
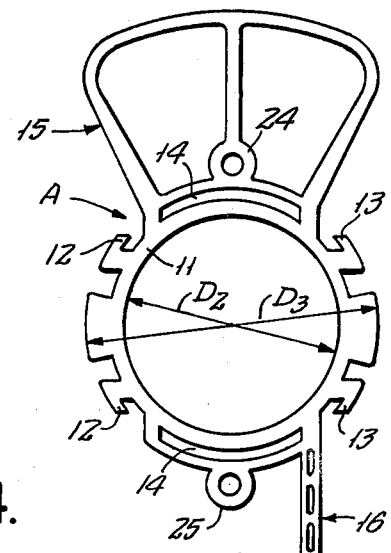
FIG. 3 is a plan view of the blank of one of the haptic parts of FIG. 1.
Figure 4:
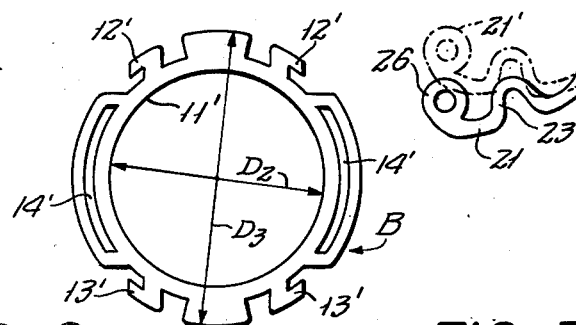
FIG. 4 is a plan view of the blank of the other of the haptic parts of FIG. 1.

In FIGS. 1 and 2, the invention is shown in application to an intraocular-lens assembly wherein an optically finished circular lens 10 is retained at its periphery by haptic or mounting-adapter structure comprising two parts A and B, each of which is separately shown, at FIGS. 3 and 4, respectively. The lens 10 is preferably of optically finished glass, with a periphery of 5-mm diameter ($D_1$); its maximum thickness $T_1$ will vary with prescription power, but such thickness is typically about 0.3-mm. Each of the haptic parts A (B) is of flexible plastic sheet material and is characterized by an annular body 11 (11') of inside diameter $D_2$ slightly less than $D_1$, to permit circumferentially continuous retaining overlap with opposite axial sides of the periphery of lens 10, when in coaxial register. The outer diameter $D_3$ of each annular body 11 (11') exceeds $D_1$ by an amount which accommodates interlocking diametrically opposed pairs of arcuate hook formations, as at 12-13 (12'-13') on one part A (B) to interlockingly engage diametrically opposed arcuate slot formations, as at 14' (14) on the other part B (A), the slot formations in each case being in quadrant interlace with the pairs of hook formations. Such formations and their interlocking are not part of the present invention, and reference is made to said copending application for more complete description thereof. The material of the haptic parts is flexible and autoclavable, being suitably a polyimide of thickness $T_2$ which may be in the range 0.05 to 0.10-mm.

In accordance with a feature of the invention, asymmetrical position-stabilizing feet 15-16 extend generally radially outward of the interlocked annular bodies 11-11' at generally diametrically opposed locations, and these feet 15-16 are integral formations of the part A alone. In the form of FIG. 1, the foot 15 is relatively stiff radially, while the foot 16 has relatively compliant radial connection to body 11. More specifically, the foot 15 is seen to comprise a generally arcuate band 17 of width $W_1$ and conforming generally to a geometrical circle having the maximum diametral span $D_4$ of part A; band 17 is integrally connected to body 11 via two outer-end legs 18-19 and via an intermediate radial leg 20. The foot 16 also comprises a generally arcuate band 21 which (when implanted) conforms generally and compliantly to the geometrical circle of diameter $D_4$, but its width $W_2$ is substantially less than $W_1$; in its unstressed state, the outer band 21 projects slightly outside the circle of diameter $D_4$ (as shown in solid outline in FIGS. 1 and 3), and when installed its compliantly deformed shape is as shown in phantom outline 21'. Radially compliant action derives from a single generally radial leg 22 (shown slotted for greater compliance) which integrally connects one end of band 21 to body 11, further radially compliant action being provided by a radially inward undulation 23 at the mid-section of band 21. A first loop formation 24 characterizes the connection of leg 20 to body 11; a second loop formation 25 is integrally formed with body 11 at a location diametrically opposed to formation 24, and a third such formation 26 is at the other angular end of the arcuate band 21. The loop formations 24-25-26 define localized circular openings of about 0.5-mm diameter, for reception of suture, pincer or other manipulating means.

When the diametral span $D_4$ is about 13-mm, depending upon internal dimensions of the posterior chamber of a particular human eye, the described lens 10 and haptic structure A-B assembled thereto is particularly suited for trans-iris operative implantation in the posterior chamber with the arcuate bands 17-21 deriving stabilizing support within the ciliary sulcus, thus placing lens 10 coaxial with the iris-to-fundus alignment and just posterior to the iris. In other words, there need be no reliance upon the iris for haptic or lens support or engagement, so that normal iris action is unimpeded, and the likelihood of related trauma is reduced to insignificance.

Various procedural options are available to the surgeon who elects to implant the assembly of FIG. 2, once he has removed all cataracted material. In one illustrative technique, he may employ a releasably tied suture filament between loops 24-26 to transiently deform foot 16 over a face of lens 10 while using a pincer hold on bodies 11-11' at the region 25, during trans-iris manipulation of foot 15 and then bodies 11-11' (and lens 10) through a dilated iris, to the point of initial band (17) contact with a local region of the ciliary sulcus. The pincer hold at region 25 is now also within the posterior chamber, and the suture retraction of foot 16 has enabled such placement with little or no interference via foot 16. The tie of suture is now released, and the suture withdrawn, thus enabling the compliant nature of foot 16 to restore itself to the phantom shape indicated in FIG. 1, namely, with posterior chamber contact and support diametrically opposed to the contact and support at 17. When satisfied that all is in desired position and angular orientation, the pincers are released and withdrawn, the operation otherwise proceeding to completion in normal fashion.

In an alternative procedure, no suture filament is required. A pincer-point insertion through loop 26 provides sufficient engagement to enable pincer-manipulated twisting of foot 16 back over a face of lens 10 prior to establishing further pincer engagement with bodies 11-11' at the region 25. Trans-iris manipulation to the point of initial band (17) contact within the ciliary sulcus is then as described above, again with little or no interference via foot 16. The pincer hold is released when the surgeon is satisfied with orientation of the initial placement, thus allowing compliant restoration of foot 16 to its stabilizing contact within the ciliary sulcus. Regardless of the technique used to achieve trans-iris posterior-chamber positioning, the loops 24-25 remain generally accessible for manipulative engagement, should further minor adjustment be deemed necessary, for correct implant positioning.

Figure 5:
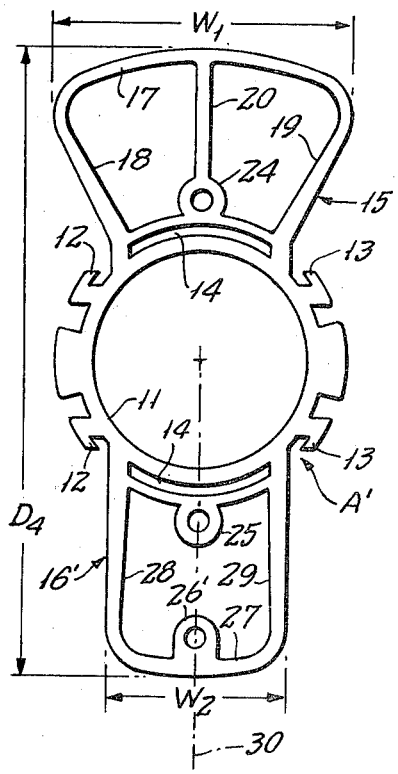
FIGS. 5, 6 and 7 are views similar to FIG. 3 to show different embodiments.

The embodiment of FIG. 5 will be seen to employ a haptic part A' in substitution of the part A of FIG. 2, lens 10 being then retained by the plural hook-and-slot engagements of part A' with those of part B. Part A' is again characterized by diametrically opposed asymmetrical feet 15-16', the arcuate band 27 of foot 16' having connection to body 11 via spaced parallel legs 28-29, and the geometric centerline 30 between legs 28-29 being radial and diametrically opposite the center leg 20 of foot 15. The third loop formation 26' is integral with the inner edge of arcuate band 27.

Manipulation and use of the FIG. 5 embodiment is as described for FIG. 2. In the event of a releasable suture filament, the tie is between loops 24-26', to hold a folded leg 16' across a face of lens 10, pincer grip and manipulation being again at the region 25. In the event of no suture filament, initial pincer engagement at loop 26' enables folded reversal of foot 16' across part of a face of lens 10, with subsequent further pincer grip at the region 25, and the pincer grip is released after the described trans-iris manipulative steps have been performed.

Figure 6:
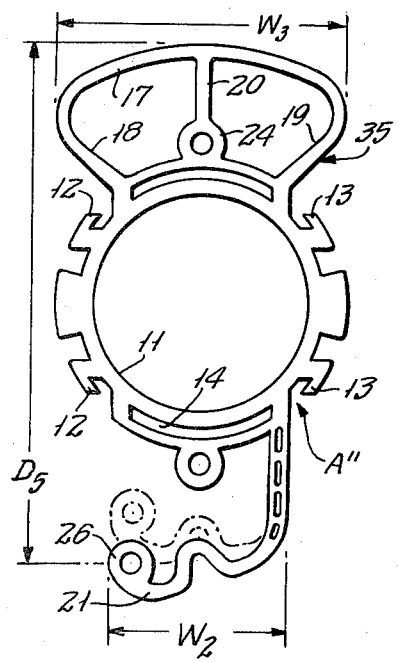
Figure 7:
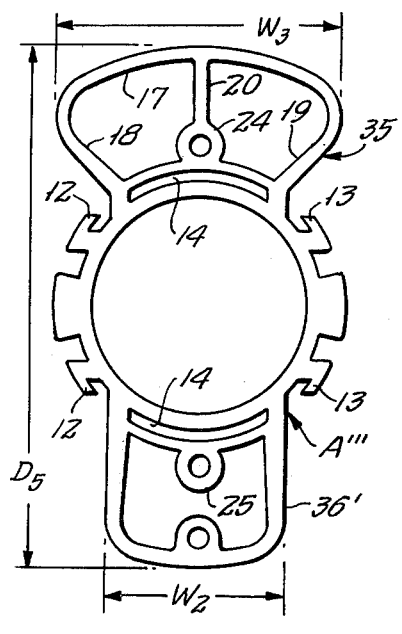

The arrangements of FIGS. 6 and 7 will be recognized for resemblance to FIGS. 1 (3) and 5, respectively, the difference being that the maximum diametral span $D_5$ is less than $D_4$. The lesser span $D_5$ enables intraocular-lens assemblies utilizing parts A" (FIG. 6) and A''' (FIG. 7) to be implanted within and to have stabilizing contact with the inner surface of a lens capsule from which cataracted material has been removed.

Dimensional legends have been applied to show commonality of general dimensions, subject to small variations which are found to characterize particular individuals. The larger width $W_1$ for the relatively stiff foot 15 (35) is preferably substantially the diametral extent $D_3$ of bodies 11-11', namely 6 to 6.5-mm, and the smaller width $W_2$ is substantially less (approximately 4.0-mm) so that when transiently folded, as described, there will assuredly be no accompanying projections of the folded foot 16 (16'-36-36') outside the outer limit of bodies 11-11'.

The described structures will be seen to have achieved all stated objects. In particular, the asymmetrical haptic configurations enable instant recognition of a reference orientation, for deliberate and correct orientation of the complete assembly in an eye, and depending upon the surgeon's predetermination of his desired ultimate orientation, whereby a lens 10 having a prescription grinding to correct for a diagnosed astigmatism error and correctly oriented for such correction in reference to the haptic asymmetry may be correctly implanted to achieve the desired correction; such techniques are explained in greater detail in my copending application Ser. No. 132,275, filed Mar. 20, 1980. The asymmetry is also seen to lend itself favorably to the mechanical problems of trans-iris implantation, whether or not releasable suture filament is employed.

While the invention has been described in detail for the preferred forms shown, it will be understood that modifications may be made without departure from the scope of the invention.

What is claimed is:

1. As an article of manufacture, an optically finished intraocular lens element having a generally circular periphery about its optical axis, and a mounting adapter for said lens element, said adapter comprising two circumferentially continuous annular body members having a circular inner edge of diameter less than the diameter of said lens element, said body members being adjacent opposite axial sides of the peripheral region of said lens element and being connected to each other within a geometrical annulus radially outside said lens element, first lens-positioning foot means extending radially outwardly of the periphery of said lens element and having radially stiff integral connection to one of said body members, and second lens-positioning foot means extending radially outwardly of the periphery of said lens element and having radially compliant integral connection to said one body member, said first and said second foot means being asymmetrically defined but in generally diametrically opposed relation to each other.

2. The article of claim 1, in which said first foot means comprises two angularly spaced generally radially extending legs integrally connected to said one body member, and a generally arcuate band integrally interconnecting the outer ends of said legs.

3. The article of claim 1, in which said second foot means comprises a single generally radially extending leg integrally connected to said one body member, and a generally arcuate band integrally connected at one end to the outer end of said leg.

4. The article of claim 2, in which said first foot means further includes a third generally radially extending leg integrally connected to said one body member and to said arcuate band at a location angularly intermediate said two angularly spaced legs.

5. As an article of manufacture, an optically finished intraocular lens element having a generally circular periphery about its optical axis, and a mounting adapter for said lens element, said adapter comprising two circumferentially continuous annular body members having a circular inner edge of diameter less than the diameter of said lens element, said body members being adjacent opposite axial sides of the peripheral region of said lens element and being connected to each other within a geometrical annulus radially outside said lens element, said body members each being of thin compliantly bendable plastic sheet material which is autoclavable and inert to body fluids, first and second asymmetrically defined lens-positioning foot means integrally formed with one of said body members and extending radially outwardly of the periphery of said lens element at generally diametrically opposed sides of the optical axis, each of said foot means comprising two angularly spaced generally radial legs and a generally arcuate band interconnecting the outer ends of said two legs.

6. The article of claim 5, in which said one body member integrally includes a first loop formation within the angular confines of one of said foot means and substantially at said geometrical annulus, and a second loop formation within the angular confines of the other of said foot means and integrally formed with the radially inner edge of the arcuate band of said other foot means, said loop formations defining localized openings adapted for reception of suture, pincer or other manipulative means.

7. The article of claim 5, in which said one body member integrally includes a first loop formation within the angular confines of one of said foot means and substantially at said geometrical annulus, and a second loop formation within the angular confines of said one foot means and integrally formed with the radially inner edge of the arcuate band of said one foot means, said loop formations defining localized openings adapted for reception of suture, pincer or other manipulative means.

8. The article of claim 6 or claim 7, in which said first loop formation is one of two substantially diametrically opposed loop formations at substantially said geometrical annulus.

9. The article of claim 5, in which the first of said foot means further includes a third generally radially extending leg integrally connected to said one body member and to said arcuate band at a location angularly intermediate the two angularly spaced legs of said first foot means.

10. The article of claim 9, in which said body member integrally includes at substantially said geometrical annulus a first loop formation connected to said third leg, and a second loop formation within the angular confines of the other of said foot means and integrally formed with the radially inner edge of the arcuate band of said other foot means, said loop formations defining localized openings adapted for reception of suture, pincer or other manipulative means.

11. As an article of manufacture, an optically finished intraocular lens element having a generally circular periphery about its optical axis, and a mounting adapter for said lens element, said adapter comprising two circumferentially continuous annular body members having a circular inner edge of diameter less than the diameter of said lens element, said body members being adjacent opposite axial sides of the peripheral region of said lens element and being connected to each other within a geometrical annulus radially outside said lens element, said body members each being of thin compliantly bendable plastic sheet material which is autoclavable and inert to body fluids, first and second asymmetrically defined lens-positioning foot means integrally formed with one of said body members and extending radially outwardly of the periphery of said lens element at generally diametrically opposed sides of the optical axis; first lens-positioning foot means comprising two angularly spaced generally radially extending legs integrally connected to said one body member, and a generally arcuate band integrally interconnecting the outer ends of said legs; and second lens-positioning foot means generally diametrically opposed to said first foot means and comprising a single generally radially extending leg integrally connected to said one body member, and a generally arcuate band integrally connected at one end to the outer end of said single leg.

12. The article of claim 11, in which said one body member integrally includes a first loop formation within the angular confines of one of said foot means and substantially at said geometrical annulus, and a second loop formation integrally formed with the other end of the arcuate band of said second foot means; said loop formations defining localized openings adapted for reception of suture, pincer or other manipulative means.

13. The article of claim 12, in which said first loop formation is one of two substantially diametrically opposed loop formations at substantially said geometrical annulus.

14. The article of claim 5 or claim 11, in which the outer diameter of said arcuate bands is no greater than substantially 13-mm, whereby said article is adapted for trans-iris placement within the ciliary sulcus of the posterior chamber of a human eye.

15. The article of claim 5 or claim 11, in which the outer diameter of said arcuate bands is no greater than substantially 11-mm, whereby said article is adapted for capsular fixation in the posterior chamber of a human eye.

16. The article of claim 5, in which the two legs of at least one of said foot means are generally parallel to each other and at equal and opposite offset from a geometrical centerline which extends radially with respect to the optical axis.

17. The article of claim 11, in which the single leg of said second foot means extends generally parallel to and at lateral offset from a geometrical radial line from the optical axis to the angular center of the arcuate band of said second foot means.

18. The article of claim 5 or claim 11, in which said lens element is of optically finished glass.

19. The article of claim 5 or claim 11, in which said plastic sheet material is a polyimide.

20. As an article of manufacture, an optically finished intraocular lens element having a generally circular periphery about its optical axis, and a mounting adapter for said lens element, said adapter comprising two circumferentially continuous annular body members having a circular inner edge of diameter less than the diameter of said lens element, said body members being adjacent opposite axial sides of the peripheral region of said lens element and being connected to each other within a geometrical annulus radially outside said lens element, said body members each being of thin compliantly bendable plastic sheet material which is autoclavable and inert to body fluids, first and second asymmetrically defined lens-positioning foot means integrally formed with one of said body members and extending radially outwardly of the periphery of said lens element at generally diametrically opposed sides of the optical axis, each of said foot means comprising a radially outer arcuate band with independent generally radial leg connection to said one body member, one of said foot means having three radial legs respectively connecting the ends and middle of the associated arcuate band to angularly spaced locations on said geometrical annulus, a first loop formation at juncture of the middle leg to said annulus, a second loop formation diametrically opposite said first loop formation, and a third loop formation integrally formed with the arcuate band of said second foot means, said loop formations defining localized openings adapted for reception of suture, pincer or other manipulative means.

21. The article of claim 20, in which the generally radial leg connection of said second foot means includes two legs spaced on opposite lateral sides of both said second and third loop formations and connected to the respective ends of the associated arcuate band.

22. The article of claim 20, in which the generally radial leg connection of said second foot means comprises a single leg connected to one end of the associated arcuate band, said third loop formation being at the other end of the associated arcuate band.

* * * * *